(12) United States Patent
Eto et al.

(10) Patent No.: US 12,251,125 B2
(45) Date of Patent: Mar. 18, 2025

(54) EXHAUST TOOL AND EXHAUST SYSTEM

(71) Applicants: Tadaaki Eto, Kagoshima (JP); TRYTEC CO., LTD, Oita (JP)

(72) Inventors: Tadaaki Eto, Kagoshima (JP); Hiroshi Takezaki, Oita (JP)

(73) Assignee: Trytec Co., Ltd., Oita (JP)

( * ) Notice: Subject to any disclaimer, the term of this patent is extended or adjusted under 35 U.S.C. 154(b) by 660 days.

(21) Appl. No.: 17/611,965

(22) PCT Filed: Mar. 25, 2021

(86) PCT No.: PCT/JP2021/012549
§ 371 (c)(1),
(2) Date: Nov. 17, 2021

(87) PCT Pub. No.: WO2021/240976
PCT Pub. Date: Dec. 2, 2021

(65) Prior Publication Data
US 2022/0304717 A1  Sep. 29, 2022

(30) Foreign Application Priority Data

May 26, 2020 (JP) .................................. 2020-091213

(51) Int. Cl.
*A61B 17/32* (2006.01)
*A61B 17/34* (2006.01)

(52) U.S. Cl.
CPC .. *A61B 17/320092* (2013.01); *A61B 17/3421* (2013.01); *A61B 2017/3445* (2013.01)

(58) Field of Classification Search
CPC .... A61B 2017/3445; A61B 2017/0046; A61B 17/3417; A61B 17/32009; A61B 18/085;

(Continued)

(56) References Cited

U.S. PATENT DOCUMENTS 5,055,100 A * 10/1991 Olsen .................. A61B 18/00
606/32
2015/0005761 A1* 1/2015 Zinnanti ............ A61B 18/1482
606/41

(Continued)

FOREIGN PATENT DOCUMENTS

CN 108135635 A 6/2018
CN 209220486 U 8/2019

(Continued)

OTHER PUBLICATIONS

Japanese Office Action issued in JP2020/091213.

(Continued)

*Primary Examiner* — Chelsea E Stinson
*Assistant Examiner* — Anh Bui
(74) *Attorney, Agent, or Firm* — Renner, Kenner, Greive, Bobak, Taylor & Weber

(57) ABSTRACT

An exhaust tool (50) includes: a flexible body portion (51) extending over substantially an entire length of a cylindrical shaft (30, 90) of an incision energy device (e.g., ultrasonic coagulation incision device 10 or electrocautery device 80) having an energy generation portion (32) for incision provided at a tip thereof; a pair of holding portions (52) provided to the body portion (51) and configured to hold the cylindrical shaft (30, 90); and a flow path formation portion (54) forming therein a flow path (56) for mist generated from the energy generation portion (32). The exhaust tool (50) is allowed to be attached/detached to/from the cylindrical shaft (30, 90) by the pair of holding portions (52) being opened through bending of the body portion (51).

8 Claims, 8 Drawing Sheets

(58) Field of Classification Search
CPC .... A61B 2018/00589; A61B 2217/005; A61B 2218/008
See application file for complete search history.

(56) References Cited

U.S. PATENT DOCUMENTS

| | | |
|---|---|---|
| 2015/0080876 A1 | 3/2015 | Worrell et al. |
| 2015/0112323 A1* | 4/2015 | Hagg ................ A61B 18/1206 606/41 |
| 2016/0114084 A1 | 4/2016 | Minskoff et al. |
| 2018/0250031 A1 | 9/2018 | Mikus et al. |

FOREIGN PATENT DOCUMENTS

| | | |
|---|---|---|
| CN | 209392086 U | 9/2019 |
| JP | 2152014 B1 | 6/2009 |
| JP | 2011523881 B2 | 12/2010 |
| JP | 2018174988 B3 | 4/2017 |
| TW | M424127 U | 3/2012 |

OTHER PUBLICATIONS

International Search Report mailed May 18, 2021 for PCT/JP2021/012549.
Taiwan Office Action dated Feb. 10, 2022 for Application No. 110112094.
Extended European Search Report dated Oct. 27, 2022 for Application No. EP 21783128.

* cited by examiner

EXHAUST TOOL AND EXHAUST SYSTEM

TECHNICAL FIELD

The present invention relates to an exhaust tool and an exhaust system.

BACKGROUND ART

In recent years, in the medical field, surgical operations have been widely performed so as to perform incision or hemostasis operation on organ tissue using an energy device such as an electrocautery or an ultrasonic coagulation incision device, while observing the inside of a body cavity using an endoscope such as a laparoscope or a thoracoscope. The proportions of laparoscopic surgery and thoracoscopic surgery in surgical operations have been increasing year by year because of their low invasiveness, good aesthetic outcome, and the like.

In performing surgery using an endoscope as described above, mist such as water vapor or smoke is generated due to heat at a part where a scalpel probe portion at the tip and organ tissue contact with each other. Such mist not only deteriorates the sight, but also adheres to the tip of the endoscope, thus causing stain on the lens thereof and deterioration of an endoscope image. Therefore, the tip of an endoscope optical tube frequently needs to be cleaned and wiped, whereby the surgery is interrupted. In order to remove the mist, generally, smoke discharge is performed via a tubular access tool (trocar sheath) for inserting a surgical instrument into the body cavity. However, since the tip of the device at which mist is generated and the smoke discharging portion of the trocar sheath are distant from each other, there is a problem that it is difficult to efficiently discharge smoke.

More specifically, information needed for surgery using an endoscope is only image (visual) information obtained from the endoscope, and sight deterioration due to generation of mist such as water vapor or smoke in the abdominal cavity, and stain on an observation window portion of the endoscope, hamper safe surgery operation. Therefore, during surgery, it takes time to wait until the mist is cleared or to extract the endoscope once to the outside of the body and clean the endoscope, so that the surgery time is prolonged, resulting in a great burden on a patient or a risk of causing an unexpected complication.

In order to solve such a problem due to mist, various devices and instruments are proposed. For example, devices for removing mist in an abdominal cavity are proposed in Japanese Laid-Open Patent Publication No. H05-329164 (JPH05-329164A), Japanese Laid-Open Patent Publication No. 2006-288754 (JP2006-288754A), Japanese Laid-Open Patent Publication No. 2017-80170 (JP2017-80170A), Japanese Laid-Open Patent Publication No. 2006-288553 (JP2006-288553A), and Japanese Laid-Open Patent Publication No. H11-309156 (JPH11-309156A). However, these are large-scale devices, require enormous cost, and require a wide installation space.

In addition, Japanese Laid-Open Patent Publication No. H8-196622 (JPH8-196622A) proposes an exhaust tube for surgery with an endoscope, but it is difficult to efficiently discharge mist in an abdominal cavity. Further, Japanese Laid-Open Patent Publication No. 2004-89510 (JP2004-89510A) and Japanese utility model registration No. 3152014 (JP3152014U) propose a smoke discharging instrument for electrocautery and an electrocautery device equipped with the same, but these are used at the time of laparotomy and are not assumed to be used in surgery inside a body cavity which is a closed space, as in surgery with an endoscope.

SUMMARY OF THE INVENTION

The present invention has been made in view of the problems of the technologies disclosed in the various conventional Patent Documents described above. That is, an object of the present invention is to provide such an exhaust tool and an exhaust system that, in performing surgery using an endoscope such as a thoracoscope or a laparoscope, in a case where the sight is deteriorated due to generation of mist such as water vapor or smoke in an abdominal cavity through usage of an incision energy device such as an ultrasonic coagulation incision device or an electrocautery device, attachment/detachment to/from a cylindrical shaft of the incision energy device can be easily performed and the generated mist can be assuredly discharged.

An exhaust tool of the present invention is an exhaust tool to be attached to a cylindrical shaft of an incision energy device having an energy generation portion for incision provided at a tip thereof, the exhaust tool including: a flexible body portion extending over substantially an entire length of the cylindrical shaft; a pair of holding portions provided to the body portion and configured to hold the cylindrical shaft; and a flow path formation portion forming therein a flow path for mist generated from the energy generation portion. The exhaust tool is allowed to be attached/detached to/from the cylindrical shaft by the pair of holding portions being opened through bending of the body portion.

In the exhaust tool of the present invention, a distance between the holding portions may be smaller than an outer diameter of the cylindrical shaft.

In addition, the body portion and the holding portions may be made of a plastic material.

In addition, at parts of the holding portions that contact with the cylindrical shaft, frictional materials may be provided for preventing a fixation position of the exhaust tool to the cylindrical shaft from being moved.

In addition, a gap may be formed between a space for holding the cylindrical shaft by the holding portions and the flow path formed by the flow path formation portion.

In addition, the exhaust tool of the present invention may further include a to-be-attached portion to which an exhaust tube is attached, and the exhaust tube attached to the to-be-attached portion may communicate with the flow path formed by the flow path formation portion.

An exhaust system of the present invention includes: an incision energy device having an energy generation portion for incision provided at a tip thereof; and an exhaust tool to be attached to a cylindrical shaft of the incision energy device. The exhaust tool includes: a flexible body portion; a pair of holding portions provided to the body portion and configured to hold the cylindrical shaft; and a flow path formation portion forming therein a flow path for mist generated from the energy generation portion. The exhaust tool is allowed to be attached/detached to/from the cylindrical shaft by the pair of holding portions being opened through bending of the body portion.

DESCRIPTION OF THE PREFERRED EMBODIMENTS

Figure 5:
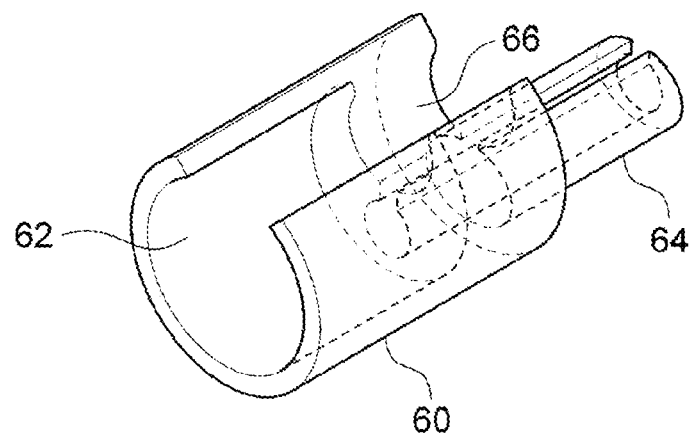
FIG. 5 is a perspective view showing the structure of a to-be-attached portion of the exhaust tool according to the embodiment of the present invention.
Figure 6:
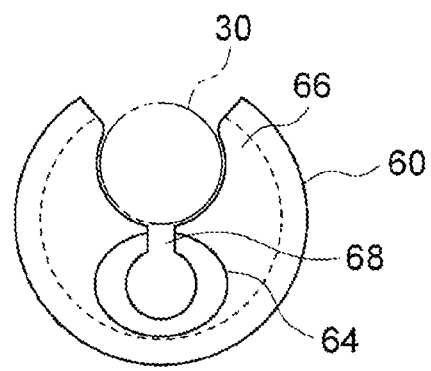
FIG. 6 is a side view showing the structure of the to-be-attached portion shown in FIG. 5, as seen from the exhaust tube connection side.
Figure 7:
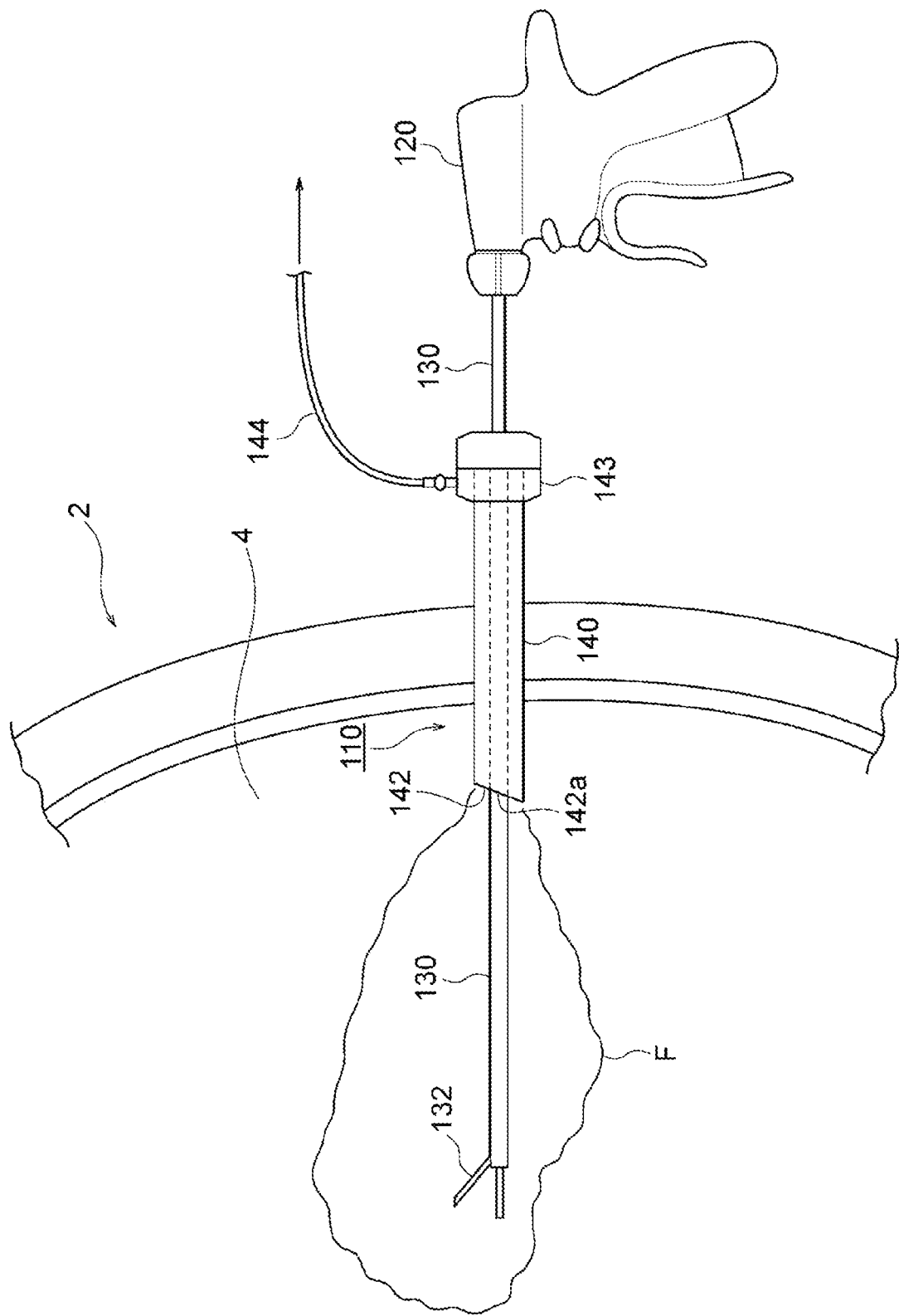
FIG. 7 is a side view of a conventional ultrasonic coagulation incision device.

Hereinafter, an embodiment of the present invention will be described with reference to the drawings. FIG. 1 to FIG. 6 show an exhaust tool according to the present embodiment and an ultrasonic coagulation incision device to which the exhaust tool is attached. FIG. 7 is a side view of a conventional ultrasonic coagulation incision device.

Figure 1:
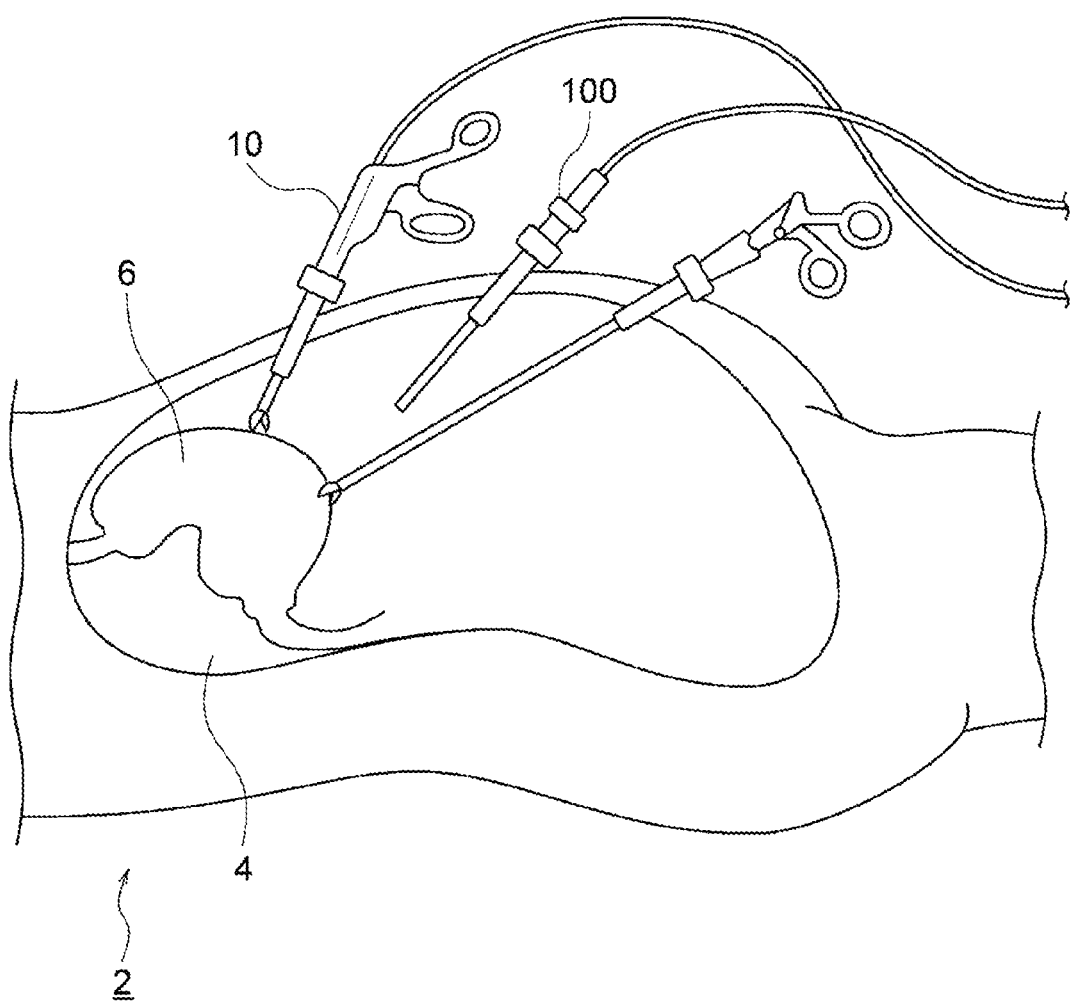
FIG. 1 schematically shows a case of performing surgery in an abdominal cavity of a human body by an ultrasonic coagulation incision device to which an exhaust tool according to an embodiment of the present invention is attached.

FIG. 1 schematically shows a case of performing surgery in an abdominal cavity 4 of a human body 2 by an ultrasonic coagulation incision device 10 to which an exhaust tool 50 according to the present embodiment is attached. As shown in FIG. 1, the ultrasonic coagulation incision device 10 and a laparoscope 100 are used in performing surgery on an organ 6 present in the abdominal cavity 4 of the human body 2, or the like. Specifically, carbon dioxide gas is injected into the abdominal cavity 4 of the human body 2 to inflate the abdominal cavity 4, and then coagulation and incision of organ tissue are performed by the ultrasonic coagulation incision device 10 while the abdominal cavity 4 of the human body 2 is observed using the laparoscope 100.

Figure 2:
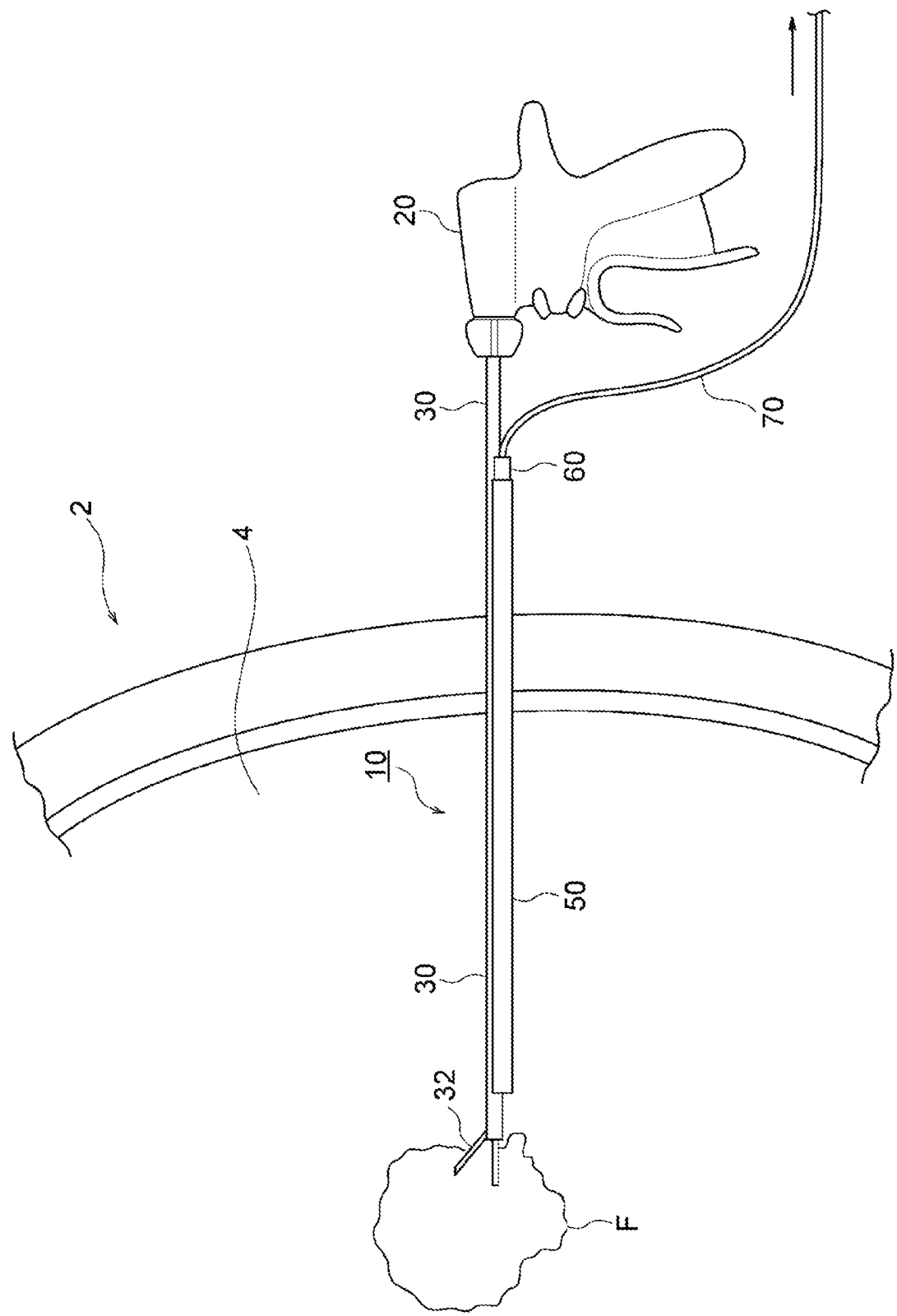
FIG. 2 is a side view of the ultrasonic coagulation incision device to which the exhaust tool according to the embodiment of the present invention is attached.
Figure 3:
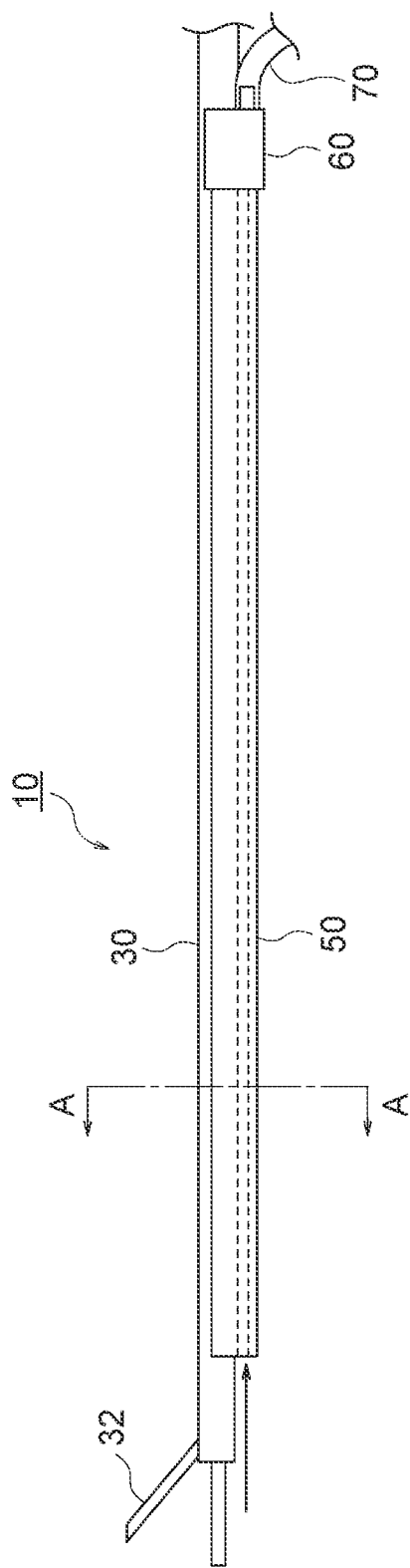
FIG. 3 is an enlarged side view of the ultrasonic coagulation incision device shown in FIG. 2.

A specific structure of the ultrasonic coagulation incision device 10 will be described with reference to FIG. 2 and FIG. 3. As shown in FIG. 2 and FIG. 3, the ultrasonic coagulation incision device 10 includes a grip portion 20 such as a handle to be gripped by a surgeon, and a cylindrical shaft 30 attached to the grip portion 20. An energy generation portion 32 for performing coagulation and incision of organ tissue is provided at the tip of the cylindrical shaft 30. Since coagulation and incision of organ tissue are performed in a state in which the energy generation portion 32 is heated, mist such as water vapor or smoke is generated from the energy generation portion 32 in the abdominal cavity 4 of the human body 2. In FIG. 2, the mist generated from the energy generation portion 32 is denoted by reference character F.

For discharging mist generated from the energy generation portion 32, an exhaust tool 50 is attached to the cylindrical shaft 30 of the ultrasonic coagulation incision device 10. In addition, an exhaust tube 70 is attached at a base end of the exhaust tool 50. A suction device (not shown) is attached to the exhaust tube 70. Through suction performed by the suction device, mist generated from the energy generation portion 32 is sucked by the exhaust tool 50 and sent from the exhaust tool 50 to the exhaust tube 70.

Figure 4:
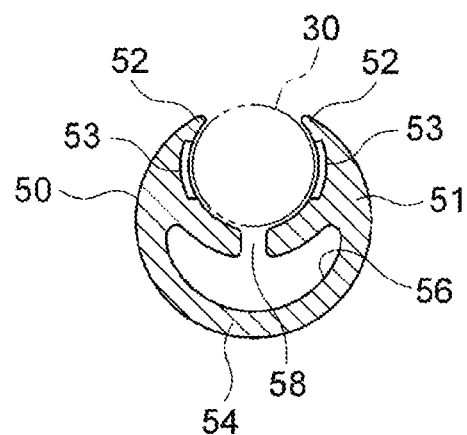
FIG. 4 is a sectional view along line A-A, of the exhaust tool attached to the ultrasonic coagulation incision device shown in FIG. 3.

FIG. 4 is a sectional view along line A-A, of the exhaust tool 50 attached to the ultrasonic coagulation incision device 10 shown in FIG. 3. As shown in FIG. 4, the exhaust tool 50 includes a flexible body portion 51 extending over substantially the entire length of the cylindrical shaft 30, a pair of holding portions 52 provided to the body portion 51 and configured to hold the cylindrical shaft 30, and a flow path formation portion 54 forming therein a flow path 56 for mist generated from the ultrasonic coagulation incision device 10. The body portion 51 is flexible and thus the exhaust tool 50 is allowed to be attached/detached to/from the cylindrical shaft 30 by the pair of holding portions 52 being opened through bending of the body portion 51.

More specifically, as shown in FIG. 4, the distance between the holding portions 52 is smaller than the diameter of the cylindrical shaft 30. Therefore, unless the distance between the holding portions 52 becomes greater than the diameter of the cylindrical shaft 30 by the body portion 51 bending, the exhaust tool 50 cannot be attached/detached to/from the cylindrical shaft 30. Thus, when the exhaust tool 50 is attached to the cylindrical shaft 30, the exhaust tool 50 does not readily come off the cylindrical shaft 30. In addition, with this structure, the surgeon can easily attach/detach the exhaust tool 50 to/from the cylindrical shaft 30.

The body portion 51 and the holding portions 52 are made of a plastic material. As shown in FIG. 2 and FIG. 3, the exhaust tool 50 extends over substantially the entire length of the cylindrical shaft 30.

At parts of the holding portions 52 that contact with the cylindrical shaft 30, frictional materials 53 are provided for preventing the fixation position of the exhaust tool 50 to the cylindrical shaft 30 from being moved. Examples of the frictional materials 53 include urethane rubber. Owing to provision of such frictional materials 53, the position of the exhaust tool 50 can be prevented from being displaced relative to the cylindrical shaft 30 during usage of the ultrasonic coagulation incision device 10.

As shown in FIG. 4, a gap 58 is formed between the space for holding the cylindrical shaft 30 by the holding portions 52 and the flow path 56 formed by the flow path formation portion 54. Owing to such a gap 58, the body portion 51 becomes more bendable, and thus the surgeon can more easily attach/detach the exhaust tool 50 to/from the cylindrical shaft 30.

The exhaust tool 50 further includes a to-be-attached portion 60 to which the exhaust tube 70 is attached. The details of the structure of the to-be-attached portion 60 will be described with reference to FIG. 5 and FIG. 6. FIG. 5 is a perspective view showing the structure of the to-be-attached portion 60. FIG. 6 is a side view showing the structure of the to-be-attached portion 60 shown in FIG. 5, as seen from the far side toward the near side.

As shown in FIG. 5 and FIG. 6, the to-be-attached portion 60 includes a body part 62, a tube attachment part 64 to which the exhaust tube 70 is attached, and a receiving part 66 for the cylindrical shaft 30. The body part 62 has a substantially C-shaped cross-section. The exhaust tube 70 can be fitted around the tube attachment part 64. A flow path for mist is formed inside the tube attachment part 64. As shown in FIG. 6, the cylindrical shaft 30 can be received by the receiving part 66. A gap 68 is formed between the area where the cylindrical shaft 30 is received by the receiving part 66 and the flow path inside the tube attachment part 64.

Next, operation of the ultrasonic coagulation incision device 10 to which the exhaust tool 50 configured as described above is attached will be described.

As described above, in performing surgery on the organ 6 present in the abdominal cavity 4 of the human body 2, or the like, carbon dioxide gas is injected into the abdominal cavity 4 of the human body 2 to inflate the abdominal cavity 4, and then coagulation and incision of organ tissue are performed by the ultrasonic coagulation incision device 10 while the abdominal cavity 4 of the human body 2 is observed using the laparoscope 100. At this time, since coagulation and incision of organ tissue are performed in a state in which the energy generation portion 32 of the ultrasonic coagulation incision device 10 is heated, mist such as water vapor or smoke is generated from the energy generation portion 32 in the abdominal cavity 4 of the human body 2 (mist generated from the energy generation portion 32 is denoted by reference character F in FIG. 2).

Meanwhile, the suction device (not shown) is attached to the exhaust tube 70. Through suction by the suction device, mist generated from the energy generation portion 32 is sucked by the exhaust tool 50 and sent from the exhaust tool 50 to the exhaust tube 70. Here, in the present embodiment, the body portion 51 of the exhaust tool 50 extends over substantially the entire length of the cylindrical shaft 30. Therefore, the tip of the exhaust tool 50 is at a position close to the energy generation portion 32 provided at the tip of the cylindrical shaft 30. Thus, mist generated from the energy generation portion 32 can be discharged by the exhaust tool 50 without widely spreading in the abdominal cavity from the energy generation portion 32.

Since mist generated from the energy generation portion 32 can be discharged from the exhaust tool 50 as described above, the sight of the laparoscope 100 can be prevented from being deteriorated by mist generated from the energy generation portion 32. Thus, it becomes unnecessary to frequently interrupt surgery for washing or cleaning an observation window portion of the laparoscope 100, so that surgery efficiency can be improved.

The exhaust tool 50 of the present embodiment configured as described above includes a flexible body portion 51 extending over substantially the entire length of the cylindrical shaft 30 of the ultrasonic coagulation incision device 10, a pair of holding portions 52 provided to the body portion 51 and configured to hold the cylindrical shaft 30, and the flow path formation portion 54 forming therein the flow path 56 for mist generated from the ultrasonic coagulation incision device 10. The exhaust tool 50 is allowed to be attached/detached to/from the cylindrical shaft 30 by the pair of holding portions 52 being opened through bending of the body portion 51. With the exhaust tool 50 as described above, since attachment/detachment to/from the cylindrical shaft 30 can be performed by the pair of holding portions 52 being opened through bending of the body portion 51, the exhaust tool 50 can be easily attached/detached to/from the ultrasonic coagulation incision device 10. Therefore, even if the flow path 56 for mist is clogged with a piece of tissue or the like, since the exhaust tool 50 can be easily detached from the cylindrical shaft 30, the exhaust tool 50 can be easily washed. In addition, generated mist can be assuredly discharged by attaching, to the cylindrical shaft 30, the exhaust tool 50 extending over substantially the entire length of the cylindrical shaft 30.

In addition, an exhaust system according to the present invention is obtained by combining the ultrasonic coagulation incision device 10 and the exhaust tool 50 described above. Also in such an exhaust system, attachment/detachment to/from the cylindrical shaft 30 can be performed by the pair of holding portions 52 being opened through bending of the body portion 51, and thus the exhaust tool 50 can be easily attached/detached to/from the ultrasonic coagulation incision device 10. In addition, generated mist can be assuredly discharged by attaching the exhaust tool 50 to the cylindrical shaft 30.

FIG. 7 is a side view of a conventional ultrasonic coagulation incision device 110. A specific structure of the conventional ultrasonic coagulation incision device 110 will be briefly described. As shown in FIG. 7, the conventional ultrasonic coagulation incision device 110 includes a grip portion 120 such as a handle to be gripped by a surgeon, and a cylindrical shaft 130 provided to the grip portion 120. An energy generation portion 132 for performing coagulation and incision of organ tissue is provided at the tip of the cylindrical shaft 130. Since coagulation and incision of organ tissue are performed in a state in which the energy generation portion 132 is heated, mist such as water vapor or smoke is generated from the energy generation portion 132 in the abdominal cavity 4 of the human body 2. In FIG. 7, the mist generated from the energy generation portion 132 is denoted by reference character F.

The ultrasonic coagulation incision device 110 is inserted into an abdominal cavity through a tubular access port 140 (trocar sheath) stuck into the abdominal cavity. As shown in FIG. 7, the access port 140 includes a cylindrical member 142 covering the cylindrical shaft 130, an attachment member 143 provided to a part of the cylindrical member 142 at the outside of the human body, and an exhaust tube 144 connected to the attachment member 143. The access port 140 is attached to the cylindrical shaft 130 by the attachment member 143. In addition, a flow path is formed inside the attachment member 143, and the internal space of the cylindrical member 142 and the exhaust tube 144 communicate with each other through the flow path.

A suction device (not shown) is attached to the exhaust tube 144. Through suction by the suction device, gas around an opening 142a provided at the tip of the cylindrical member 142 passes through the flow path inside the cylindrical member 142 and is sent from the attachment member 143 to the exhaust tube 144.

In the ultrasonic coagulation incision device 110 shown in FIG. 7, the opening 142a provided at the tip of the cylindrical member 142 is at a position far from the tip of the cylindrical shaft 130, and thus there is a problem that mist generated from the energy generation portion 132 spreads before entering the opening 142a.

In contrast, in the case where the exhaust tool 50 of the present embodiment is attached to the ultrasonic coagulation incision device 10, the above problem of the conventional exhaust system can be solved.

The exhaust tool according to the present invention is not limited to the above-described structure, and may be modified in various manners.

Figure 8:
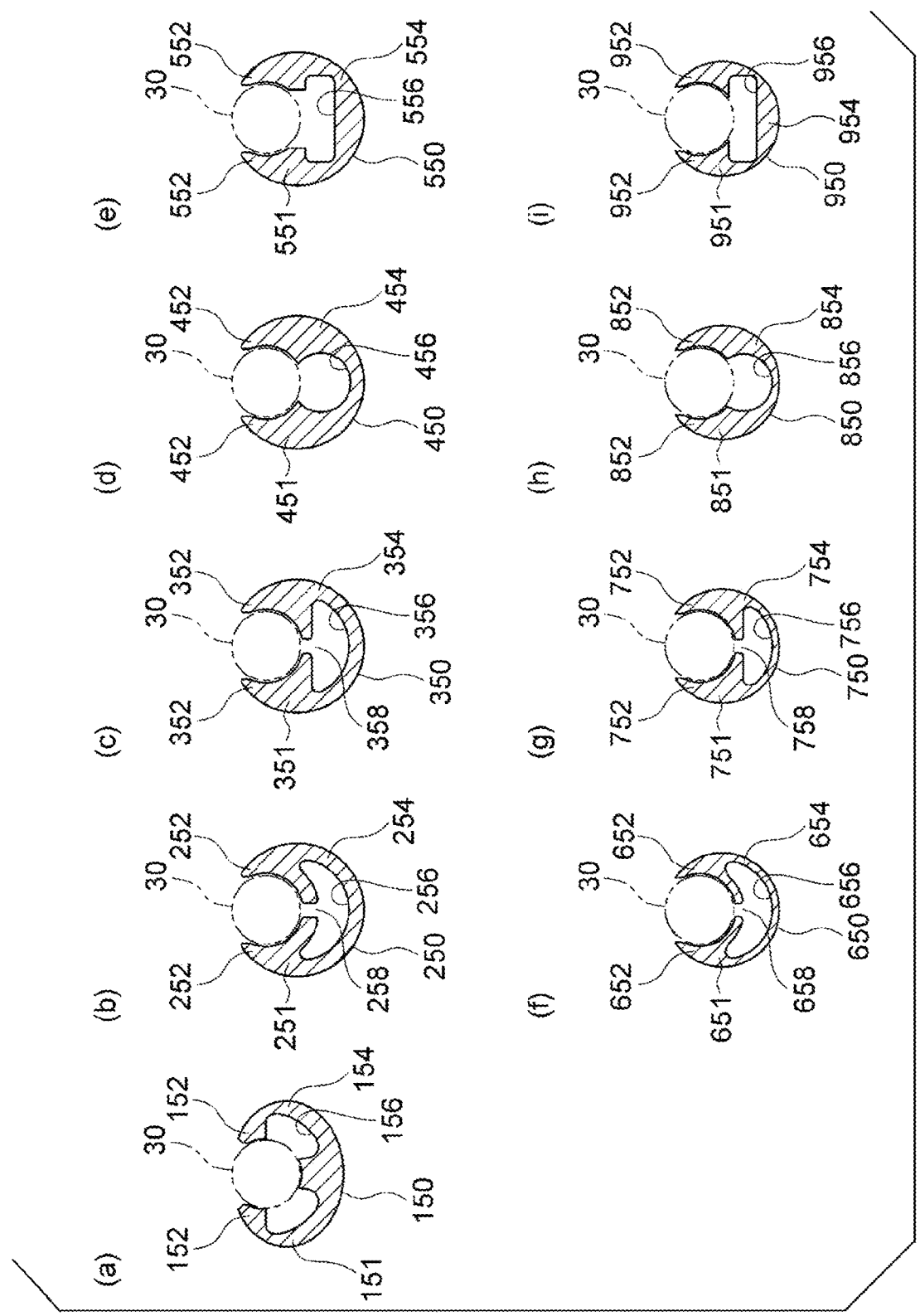
FIG. 8 of series (a) to (i) is each of sectional views of exhaust tools having various other structures according to the present invention.

For example, the cross-section of the exhaust tool is not limited to the shape shown in FIG. 4. FIG. 8 of (a) to (i) is each of sectional views of exhaust tools having various other structures according to the present invention.

An exhaust tool 150 shown in FIG. 8(a) includes a flexible body portion 151 extending over substantially the entire length of the cylindrical shaft 30, a pair of holding portions 152 provided to the body portion 151 and configured to hold the cylindrical shaft 30, and a flow path formation portion 154 forming therein two flow paths 156 for mist generated from the tip of the ultrasonic coagulation incision device 10. The exhaust tool 150 is allowed to be attached/detached to/from the cylindrical shaft 30 by the pair of holding portions 152 being opened through bending of the body portion 151. More specifically, as shown in FIG. 8(*a*), the distance between the holding portions 152 is smaller than the diameter of the cylindrical shaft 30. Therefore, unless the distance between the holding portions 152 becomes greater than the diameter of the cylindrical shaft 30 by the body portion 151 bending, the exhaust tool 150 cannot be attached/detached to/from the cylindrical shaft 30. The body portion 151 and the holding portions 152 are made of a plastic material. The space for holding the cylindrical shaft 30 by the holding portions 152 communicates with each of the two flow paths 156 formed by the flow path formation portion 154.

An exhaust tool 250 shown in FIG. 8(*b*) includes a flexible body portion 251 extending over substantially the entire length of the cylindrical shaft 30, a pair of holding portions 252 provided to the body portion 251 and configured to hold the cylindrical shaft 30, and a flow path formation portion 254 forming therein a flow path 256 for mist generated from the tip of the ultrasonic coagulation incision device 10. The exhaust tool 250 is allowed to be attached/detached to/from the cylindrical shaft 30 by the pair of holding portions 252 being opened through bending of the body portion 251. More specifically, as shown in FIG. 8(*b*), the distance between the holding portions 252 is smaller than the diameter of the cylindrical shaft 30. Therefore, unless the distance between the holding portions 252 becomes greater than the diameter of the cylindrical shaft 30 by the body portion 251 bending, the exhaust tool 250 cannot be attached/detached to/from the cylindrical shaft 30. The body portion 251 and the holding portions 252 are made of a plastic material. A gap 258 is formed between the space for holding the cylindrical shaft 30 by the holding portions 252 and the flow path 256 formed by the flow path formation portion 254.

An exhaust tool 350 shown in FIG. 8(*c*) includes a flexible body portion 351, a pair of holding portions 352 provided to the body portion 351 and configured to hold the cylindrical shaft 30, and a flow path formation portion 354 forming therein a flow path 356 for mist generated from the tip of the ultrasonic coagulation incision device 10. The exhaust tool 350 is allowed to be attached/detached to/from the cylindrical shaft 30 by the pair of holding portions 352 being opened through bending of the body portion 351. More specifically, as shown in FIG. 8(*c*), the distance between the holding portions 352 is smaller than the diameter of the cylindrical shaft 30. Therefore, unless the distance between the holding portions 352 becomes greater than the diameter of the cylindrical shaft 30 by the body portion 351 bending, the exhaust tool 350 cannot be attached/detached to/from the cylindrical shaft 30. The body portion 351 and the holding portions 352 are made of a plastic material. A gap 358 is formed between the space for holding the cylindrical shaft 30 by the holding portions 352 and the flow path 356 formed by the flow path formation portion 354.

An exhaust tool 450 shown in FIG. 8(*d*) includes a flexible body portion 451 extending over substantially the entire length of the cylindrical shaft 30, a pair of holding portions 452 provided to the body portion 451 and configured to hold the cylindrical shaft 30, and a flow path formation portion 454 forming therein a flow path 456 for mist generated from the tip of the ultrasonic coagulation incision device 10. The exhaust tool 450 is allowed to be attached/detached to/from the cylindrical shaft 30 by the pair of holding portions 452 being opened through bending of the body portion 451. More specifically, as shown in FIG. 8(*d*), the distance between the holding portions 452 is smaller than the diameter of the cylindrical shaft 30. Therefore, unless the distance between the holding portions 452 becomes greater than the diameter of the cylindrical shaft 30 by the body portion 451 bending, the exhaust tool 450 cannot be attached/detached to/from the cylindrical shaft 30. The body portion 451 and the holding portions 452 are made of a plastic material. The space for holding the cylindrical shaft 30 by the holding portions 452 communicates with the flow path 456 formed by the flow path formation portion 454.

An exhaust tool 550 shown in FIG. 8(*e*) includes a flexible body portion 551 extending over substantially the entire length of the cylindrical shaft 30, a pair of holding portions 552 provided to the body portion 551 and configured to hold the cylindrical shaft 30, and a flow path formation portion 554 forming therein a flow path 556 for mist generated from the tip of the ultrasonic coagulation incision device 10. The exhaust tool 550 is allowed to be attached/detached to/from the cylindrical shaft 30 by the pair of holding portions 552 being opened through bending of the body portion 551. More specifically, as shown in FIG. 8(*e*), the distance between the holding portions 552 is smaller than the diameter of the cylindrical shaft 30. Therefore, unless the distance between the holding portions 552 becomes greater than the diameter of the cylindrical shaft 30 by the body portion 551 bending, the exhaust tool 550 cannot be attached/detached to/from the cylindrical shaft 30. The body portion 551 and the holding portions 552 are made of a plastic material. The space for holding the cylindrical shaft 30 by the holding portions 552 communicates with the flow path 556 formed by the flow path formation portion 554.

An exhaust tool 650 shown in FIG. 8(*f*) includes a flexible body portion 651, a pair of holding portions 652 provided to the body portion 651 and configured to hold the cylindrical shaft 30, and a flow path formation portion 654 forming therein a flow path 656 for mist generated from the tip of the ultrasonic coagulation incision device 10. The exhaust tool 650 is allowed to be attached/detached to/from the cylindrical shaft 30 by the pair of holding portions 652 being opened through bending of the body portion 651. More specifically, as shown in FIG. 8(*f*), the distance between the holding portions 652 is smaller than the diameter of the cylindrical shaft 30. Therefore, unless the distance between the holding portions 652 becomes greater than the diameter of the cylindrical shaft 30 by the body portion 651 bending, the exhaust tool 650 cannot be attached/detached to/from the cylindrical shaft 30. The body portion 651 and the holding portions 652 are made of a plastic material. A gap 658 is formed between the space for holding the cylindrical shaft 30 by the holding portions 652 and the flow path 656 formed by the flow path formation portion 654.

An exhaust tool 750 shown in FIG. 8(*g*) includes a flexible body portion 751, a pair of holding portions 752 provided to the body portion 751 and configured to hold the cylindrical shaft 30, and a flow path formation portion 754 forming therein a flow path 756 for mist generated from the tip of the ultrasonic coagulation incision device 10. The exhaust tool 750 is allowed to be attached/detached to/from the cylindrical shaft 30 by the pair of holding portions 752 being opened through bending of the body portion 751. More specifically, as shown in FIG. 8(*g*), the distance between the holding portions 752 is smaller than the diameter of the cylindrical shaft 30. Therefore, unless the distance between the holding portions 752 becomes greater than the diameter of the cylindrical shaft 30 by the body portion 751 bending, the exhaust tool 750 cannot be attached/detached to/from the cylindrical shaft 30. The body portion 751 and the holding portions 752 are made of a plastic material. A gap 758 is formed between the space for holding the cylindrical shaft 30 by the holding portions 752 and the flow path 756 formed by the flow path formation portion 754.

An exhaust tool 850 shown in FIG. 8(*h*) includes a flexible body portion 851, a pair of holding portions 852 provided to the body portion 851 and configured to hold the cylindrical shaft 30, and a flow path formation portion 854 forming therein a flow path 856 for mist generated from the tip of the ultrasonic coagulation incision device 10. The exhaust tool 850 is allowed to be attached/detached to/from the cylindrical shaft 30 by the pair of holding portions 852 being opened through bending of the body portion 851. More specifically, as shown in FIG. 8(*h*), the distance between the holding portions 852 is smaller than the diameter of the cylindrical shaft 30. Therefore, unless the distance between the holding portions 852 becomes greater than the diameter of the cylindrical shaft 30 by the body portion 851 bending, the exhaust tool 850 cannot be attached/detached to/from the cylindrical shaft 30. The body portion 851 and the holding portions 852 are made of a plastic material. The space for holding the cylindrical shaft 30 by the holding portions 852 communicates with the flow path 856 formed by the flow path formation portion 854.

An exhaust tool 950 shown in FIG. 8(*i*) includes a flexible body portion 951 extending over substantially the entire length of the cylindrical shaft 30, a pair of holding portions 952 provided to the body portion 951 and configured to hold the cylindrical shaft 30, and a flow path formation portion 954 forming therein a flow path 956 for mist generated from the tip of the ultrasonic coagulation incision device 10. The exhaust tool 950 is allowed to be attached/detached to/from the cylindrical shaft 30 by the pair of holding portions 952 being opened through bending of the body portion 951. More specifically, as shown in FIG. 8(*i*), the distance between the holding portions 952 is smaller than the diameter of the cylindrical shaft 30. Therefore, unless the distance between the holding portions 952 becomes greater than the diameter of the cylindrical shaft 30 by the body portion 951 bending, the exhaust tool 950 cannot be attached/detached to/from the cylindrical shaft 30. The body portion 951 and the holding portions 952 are made of a plastic material. The space for holding the cylindrical shaft 30 by the holding portions 952 communicates with the flow path 956 formed by the flow path formation portion 954.

Figure 9:
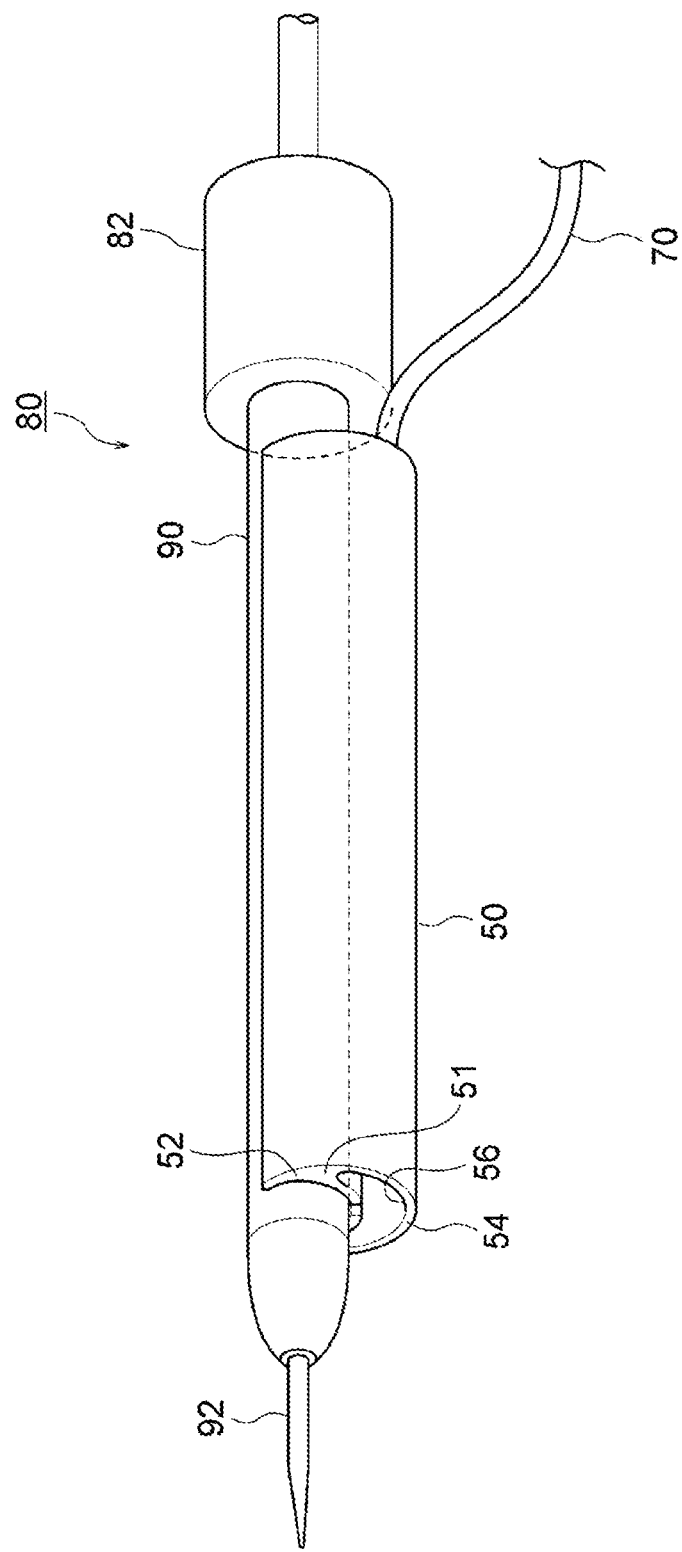
FIG. 9 is a perspective view of an electrocautery device to which the exhaust tool according to the present invention is attached.

The exhaust tool according to the present invention is not limited to the one to be attached to the ultrasonic coagulation incision device 10. The exhaust tool according to the present invention may be attached to an incision energy device other than the ultrasonic coagulation incision device 10. FIG. 9 is a perspective view of an electrocautery device 80 (incision energy device) to which the exhaust tool 50 according to the present invention is attached. The exhaust tool 50 attached to the electrocautery device 80 shown in FIG. 9 has the same structure as the exhaust tool 50 shown in FIG. 1 to FIG. 6, and therefore the description thereof is omitted.

The electrocautery device 80 includes a grip portion 82 to be gripped by a surgeon, and a cylindrical shaft 90 attached to the grip portion 82. An energy generation portion 92 for performing coagulation and incision of organ tissue is provided at the tip of the cylindrical shaft 90. Since coagulation and incision of a blood vessel or tissue are performed in a state in which the energy generation portion 92 is heated, mist such as water vapor or smoke is generated from the energy generation portion 92 in the abdominal cavity 4 of the human body 2.

For discharging mist generated from the energy generation portion 92, the exhaust tool 50 is attached to the cylindrical shaft 90 of the electrocautery device 80. In addition, the exhaust tube 70 is attached at a base end of the exhaust tool 50. A suction device (not shown) is attached to the exhaust tube 70. Through suction performed by the suction device, mist generated from the energy generation portion 92 is sucked by the exhaust tool 50 and sent from the exhaust tool 50 to the exhaust tube 70.

As shown in FIG. 9, also in the case where the exhaust tool 50 is attached to the electrocautery device 80, the exhaust tool 50 includes the flexible body portion 51 extending over substantially the entire length of the cylindrical shaft 90 of the electrocautery device 80, the pair of holding portions 52 provided to the body portion 51 and configured to hold the cylindrical shaft 90, and the flow path formation portion 54 forming therein the flow path 56 for mist generated from the tip of the electrocautery device 80. The exhaust tool 50 is allowed to be attached/detached to/from the cylindrical shaft 90 by the pair of holding portions 52 being opened through bending of the body portion 51. With the exhaust tool 50 as described above, since attachment/detachment to/from the cylindrical shaft 90 can be performed by the body portion 51 bending, the exhaust tool 50 can be easily attached/detached to/from the electrocautery device 80. In addition, generated mist can be assuredly discharged by attaching, to the cylindrical shaft 90, the exhaust tool 50 extending over substantially the entire length of the cylindrical shaft 90.

In addition, an exhaust system according to the present invention is obtained by combining the electrocautery device 80 and the exhaust tool 50 described above. Also in such an exhaust system, attachment/detachment to/from the cylindrical shaft 90 can be performed by the body portion 51 bending, and thus the exhaust tool 50 can be easily attached/detached to/from the electrocautery device 80. In addition, generated mist can be assuredly discharged by attaching the exhaust tool 50 to the cylindrical shaft 90.

The exhaust tool of the present invention can be attached to various types of incision energy devices, besides the ultrasonic coagulation incision device 10 and the electrocautery device 80 described above as incision energy devices, as long as the shaft to which the exhaust tool is attached has a cylindrical shape.

The invention claimed is:

1. An exhaust tool to be attached to a cylindrical shaft of an incision energy device having an energy generation portion for incision provided at a tip thereof, the exhaust tool comprising:
   a flexible body portion configured to extend over substantially an entire length of the cylindrical shaft;
   the flexible body portion including a pair of holding portions configured to hold the cylindrical shaft, the pair of holding portions extending over substantially the entire length of the cylindrical shaft; and
   a flow path formation portion forming therein a flow path for mist generated from the energy generation portion, wherein
   the exhaust tool is configured to be attached/detached to/from the cylindrical shaft by the pair of holding portions being opened through bending of the flexible body portion.

2. The exhaust tool according to claim 1, wherein
   a distance between the pair of holding portions is smaller than an outer diameter of the cylindrical shaft.

3. The exhaust tool according to claim 1, wherein the flexible body portion and the pair of holding portions are made of a plastic material.

4. The exhaust tool according to claim 1, wherein at parts of the pair of holding portions that are in contact with the cylindrical shaft, frictional materials are provided for preventing the exhaust tool from being moved relative to the cylindrical shaft.

5. The exhaust tool according to claim 1, wherein a gap is formed between a space for holding the cylindrical shaft by the pair of holding portions and the flow path formed by the flow path formation portion.

6. The exhaust tool according to claim 1, further comprising a to-be-attached portion to which an exhaust tube is attached, wherein
the exhaust tube attached to the to-be-attached portion communicates with the flow path formed by the flow path formation portion.

7. An exhaust system comprising:
an incision energy device having an energy generation portion for incision provided at a tip thereof; and
an exhaust tool to be attached to a cylindrical shaft of the incision energy device, wherein the exhaust tool includes
a flexible body portion,
the flexible body portion including a pair of holding portions configured to hold the cylindrical shaft, the pair of holding portions extending over substantially the entire length of the cylindrical shaft, and
a flow path formation portion forming therein a flow path for mist generated from the energy generation portion, and
the exhaust tool is configured to be attached/detached to/from the cylindrical shaft by the pair of holding portions being opened through bending of the flexible body portion.

8. An exhaust tool to be attached to a cylindrical shaft of an incision energy device having an energy generation portion for incision provided at a tip thereof, the exhaust tool comprising:
a flexible body portion configured to extend over substantially an entire length of the cylindrical shaft;
the flexible body portion including a pair of holding portions configured to hold the cylindrical shaft; and
a flow path formation portion, wherein the exhaust tool is configured to be attached/detached to/from the cylindrical shaft by the pair of holding portions being opened through bending of the flexible body portion, and, when the exhaust tool is attached to the cylindrical shaft, the flow path formation portion and the cylindrical shaft define a flow path for mist generated from the energy generation portion, the cylindrical shaft completing a boundary of the flow path with the flow path formation portion.

* * * * *